(12) United States Patent
Glozman et al.

(10) Patent No.: US 9,072,602 B2
(45) Date of Patent: Jul. 7, 2015

(54) TRANSCATHETER VALVE PROSTHESIS HAVING A VARIABLE SHAPED CROSS-SECTION FOR PREVENTING PARAVALVULAR LEAKAGE

(71) Applicant: Medtronic, Inc., Minneapolis, MN (US)

(72) Inventors: Daniel Glozman, Netanya (IL); Igor Kovalsky, Mounds View, MN (US); Jason Quill, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 219 days.

(21) Appl. No.: 13/676,286

(22) Filed: Nov. 14, 2012

(65) Prior Publication Data

US 2014/0135908 A1 May 15, 2014

(51) Int. Cl.
*A61F 2/24* (2006.01)

(52) U.S. Cl.
CPC ............. *A61F 2/2412* (2013.01); *A61F 2/2418* (2013.01); *A61F 2/2475* (2013.01); *A61F 2230/0023* (2013.01); *A61F 2230/0078* (2013.01); *A61F 2230/008* (2013.01); *A61F 2220/0075* (2013.01); *A61F 2230/0054* (2013.01)

(58) Field of Classification Search
CPC ... A61F 2/2427; A61F 2/2436; A61F 2/2433; A61F 2/243
USPC ............ 623/2.18, 2.17, 1.12, 1.11, 2.19, 2.11
See application file for complete search history.

(56) References Cited

U.S. PATENT DOCUMENTS

| | | | |
|---|---|---|---|
| 5,957,949 A | 9/1999 | Leonhardt et al. | |
| 6,454,799 B1 * | 9/2002 | Schreck | 623/2.18 |
| 7,276,078 B2 | 10/2007 | Spenser et al. | |
| 7,780,725 B2 | 8/2010 | Haug et al. | |
| 2003/0199963 A1 | 10/2003 | Tower et al. | |
| 2003/0199971 A1 | 10/2003 | Tower et al. | |
| 2004/0111111 A1 | 6/2004 | Lin | |
| 2007/0293944 A1 | 12/2007 | Spenser et al. | |
| 2008/0071361 A1 | 3/2008 | Tuval et al. | |
| 2008/0071362 A1 * | 3/2008 | Tuval et al. | 623/2.1 |
| 2008/0243245 A1 | 10/2008 | Thambar et al. | |
| 2009/0099653 A1 | 4/2009 | Suri et al. | |
| 2010/0036479 A1 | 2/2010 | Hill et al. | |
| 2010/0168844 A1 | 7/2010 | Toomes et al. | |
| 2010/0262231 A1 | 10/2010 | Tuval et al. | |
| 2011/0054466 A1 | 3/2011 | Rothstein et al. | |
| 2011/0098802 A1 | 4/2011 | Braido et al. | |
| 2011/0160836 A1 * | 6/2011 | Behan | 623/1.11 |
| 2011/0172765 A1 | 7/2011 | Nguyen et al. | |
| 2011/0264206 A1 | 10/2011 | Tabor | |
| 2012/0158129 A1 | 6/2012 | Duffy et al. | |

* cited by examiner

*Primary Examiner* — Jonathan W Miles
*Assistant Examiner* — George J Ulsh

(57) ABSTRACT

A transcatheter valve prosthesis includes a self-expanding tubular stent component and a prosthetic valve disposed within and secured to the stent component. The tubular stent component has a proximal portion, a distal portion, and an intermediate portion between the proximal and distal portions. In a compressed delivery configuration, the tubular stent component has a generally circular cross-section along its length. In an expanded deployed configuration, the proximal and distal portions have a generally circular cross-section while the intermediate portion of the stent component has a generally triangular cross-section with three vertexes that are configured to project into three commissural points of a native valve when the valve prosthesis is implanted in situ. The generally triangular transverse cross-section of the valve prosthesis is formed by pulling or extending selected or particular struts of the stent component radially outwards and then applying heat to heat-set the stent component in the deployed configuration.

18 Claims, 9 Drawing Sheets

TRANSCATHETER VALVE PROSTHESIS HAVING A VARIABLE SHAPED CROSS-SECTION FOR PREVENTING PARAVALVULAR LEAKAGE

FIELD OF THE INVENTION

Embodiments hereof relate to transcatheter valve prostheses that prevent paravalvular leakage. More specifically, the present invention relates to a transcatheter valve prosthesis having a variable shaped cross-section along its length to prevent paravalvular leakage.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible endoluminal prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods are intended to provide safer and less invasive methods for replacing a defective native heart valve, leakage between the implanted prosthetic valve and the surrounding native tissue is a concern. Preventing leakage at the commissural points of the native valve leaflets is of particular concern as at each commissural point, a gap may exist between the expanded prosthetic valve frame and the wall of the native annulus. More particularly, FIG. 1 illustrates a cross-sectional view of a heart having an aortic valve AV, with arrows indicating the direction of blood flow through the aortic valve AV from the left ventricle LV into the aorta A. FIG. 2 is a cut-away view illustrating the general anatomy of the aortic valve AV extending between the left ventricle LV into the aorta A. The aortic valve AV includes a first or proximal region including a virtual basal ring or a native valve annulus $A_N$ and a second or distal region including three native valve leaflets $L_N$, although only two leaflets are shown in the cutaway view of FIG. 2. As illustrated, the proximal region or valve annulus $A_N$ has a generally circular cross-section $C_C$ while the distal region or area between the native valve leaflets $L_N$ is not circular but rather has a generally triangular cross-section $C_T$. The vertexes of the generally triangular cross-section correspond to the commissural points CP of the native valve leaflets $L_N$.

FIG. 3 is a top-down view of the aortic valve AV with a prosthetic heart valve 300 implanted therein. Prosthetic heart valve 300 has a circular cross-sectional along an entire length thereof. When expanded within the native valve leaflets $L_N$, the outer surface of prosthetic heart valve 300 does not provide an exact fit in the area between the native valve leaflets $L_N$. Gaps 302 may form or be present between a perimeter or outer surface of prosthetic heart valve 300 and the surrounding native tissue, particularly at the commissural points CP of the native valve leaflets $L_N$. As the prosthetic valve assumes responsibility for regulating blood flow through the native valve, gaps 302 can make it difficult for prosthetic heart valve 300 to form a blood tight seal between the prosthetic valve and the native tissue, causing undesirable paravalvular leakage and/or regurgitation at the implantation site.

Embodiments hereof are related to a transcatheter valve prosthesis having a variable or non-uniform shaped cross-section along its length to prevent paravalvular leakage.

BRIEF SUMMARY OF THE INVENTION

Embodiments hereof relate to a valve prosthesis including a tubular stent component defining a lumen therethrough and having a compressed delivery configuration for transcatheter delivery within a vasculature and a deployed configuration for implantation within a native heart valve. In the delivery configuration, the tubular stent component has a generally circular cross-section along its length. In the deployed configuration, the tubular stent component includes a first portion having a generally circular cross-section and a second portion having a generally triangular cross-section. A prosthetic valve component is disposed within and secured to the stent component.

Embodiments hereof also relate to a transcatheter valve prosthesis including a tubular self-expanding stent component defining a lumen therethrough and having a deployed configuration for implantation within a native heart valve. The tubular stent component has a proximal portion, a distal portion, and an intermediate portion between the proximal and distal portions. The tubular stent component has a variable shaped cross-section when in the deployed configuration in which at least the intermediate portion has a generally triangular cross-section with three vertexes that are configured to project into three commissural points of a native valve when the valve prosthesis is implanted in situ. A prosthetic valve component is disposed within and secured to the stent component, wherein the prosthetic valve component includes three valve leaflets.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to the heart. "Distal" or "distally" are a position or in a direction away from the heart and "proximal" and "proximally" are a position near or in a direction toward the heart. Regarding "proximal" and "distal" positions referenced herein, a proximal end of a prosthesis is the end closest to the heart by way of blood flow path whereas a distal end of the prosthesis is the end furthest away from the heart during deployment.

The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. Furthermore, there is no intention to be bound by any expressed or implied theory presented in the preceding technical field, background, brief summary or the following detailed description.

Embodiments hereof relate to a transcatheter valve prosthesis that prevents or minimizes paravalvular leakage by having a cross-sectional shape that varies or is non-uniform along a length of the prosthesis in a deployed or expanded configuration. The valve prosthesis includes a portion having a generally triangular cross-section that conforms to or imitates the shape of the native heart valve, particularly at the location of the commissural points of the native valve leaflets, to substantially prevent gaps between the perimeter of a heart valve prosthesis and the native valve tissue. "Substantially prevents gaps" as utilized herein means that blood flow between the perimeter of a deployed heart valve prosthesis and the native valve tissue is occluded or blocked, or stated another way blood is not permitted to flow there through.

Figure 1:
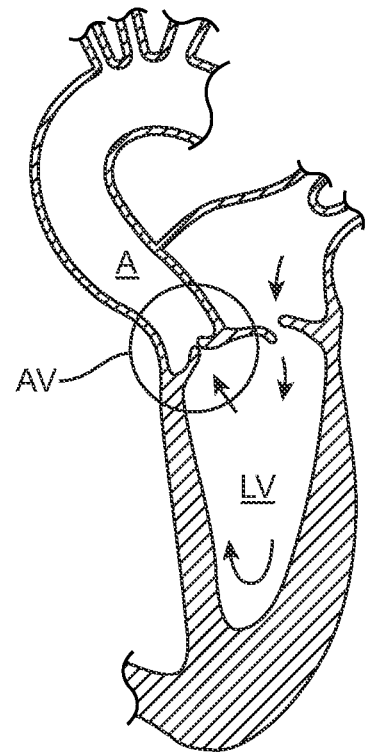
FIG. 1 illustrates a sectional view of a heart having an aortic valve AV, with arrows indicating the direction of blood flow through of the aortic valve AV.
Figure 2:
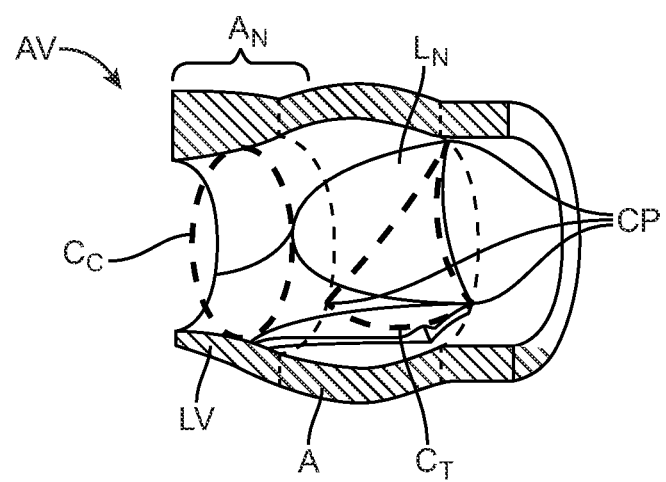
FIG. 2 is a cut-away view illustrating the general anatomy of the aortic valve AV.
Figure 3:
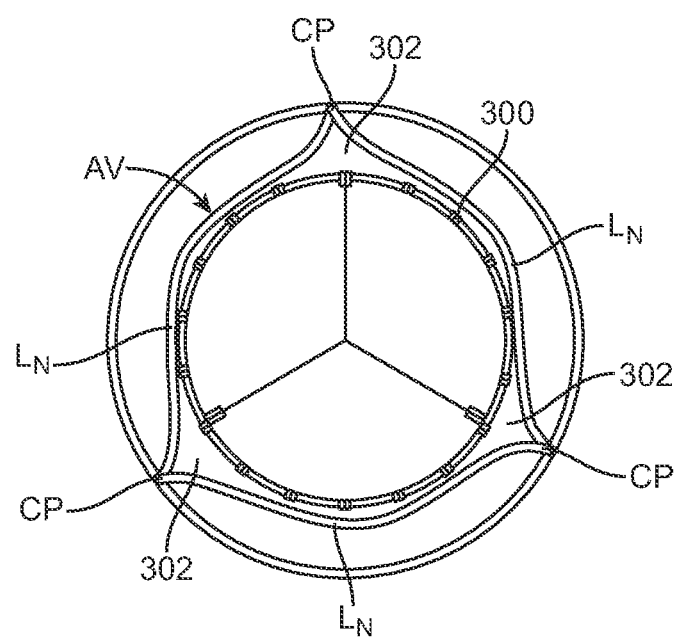
FIG. 3 is a top-down view of an aortic valve AV with an exemplary prior art prosthetic heart valve implanted therein.
Figure 4:
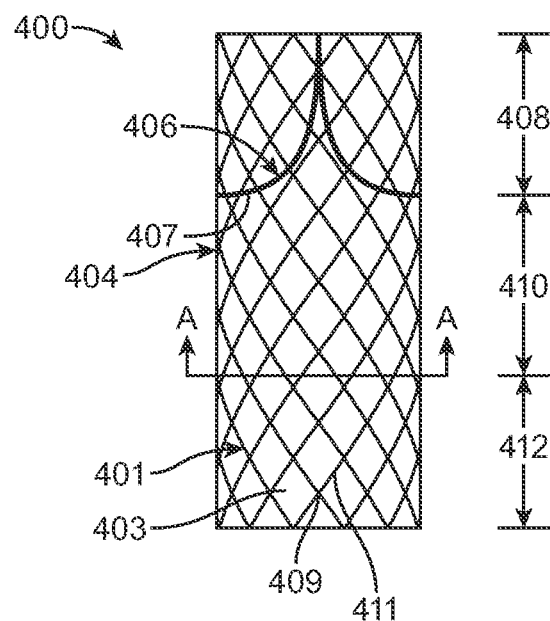
FIG. 4 is a side view of a heart valve prosthesis according to an embodiment hereof, wherein the heart valve prosthesis is depicted in a compressed, delivery configuration.

FIG. 4 illustrates a transcatheter heart valve prosthesis 400 according to an embodiment hereof. Heart valve prosthesis 400 includes an expandable stent component 404 that supports a prosthetic valve component 406 within the interior of stent component 404. Stent component 404 is a generally tubular support structure that defines a lumen 405 therethrough. Stent component 404 includes a framework 401 that defines a plurality of diamond or kite-shaped openings 403. Each diamond-shaped opening 403 is defined by four vertexes or vertices 409 and four segments or struts 411 extending or formed between vertexes 409. In this embodiment, framework 401 has a lattice configuration which is laser cut from a tube and is formed as a unitary structure or component. In embodiments hereof, stent component 404 has a shape memory to self-expand or return to an expanded or deployed state shown in FIG. 5 from a compressed or delivery state shown in FIG. 4 and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent component 404 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety.

Prosthetic valve component 406 of valve prosthesis 400 is capable of blocking flow in one direction to regulate flow there through via three valve leaflets 407 that form a tricuspid replacement valve. More particularly, heart valve prosthesis 400 is configured for placement within a native valve having three leaflets such as the aortic, tricuspid, or pulmonary valves. Valve leaflets 407 are sutured or otherwise securely and sealingly attached to the interior surface of stent component 404 and/or graft material (not shown in FIG. 4) which encloses or lines stent component 404 as would be known to one of ordinary skill in the art of prosthetic tissue valve construction.

Leaflets 407 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 407 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Similarly, a graft material (not shown) for use with valve prosthesis 400 may also be a natural or biological material such as pericardium or another membranous tissue such as intestinal submucosa. Alternatively, the graft material may be a low-porosity woven fabric, such as polyester, Dacron fabric, or PTFE, which creates a one-way fluid passage when attached to the stent component. In one embodiment, the graft material may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Figure 5:
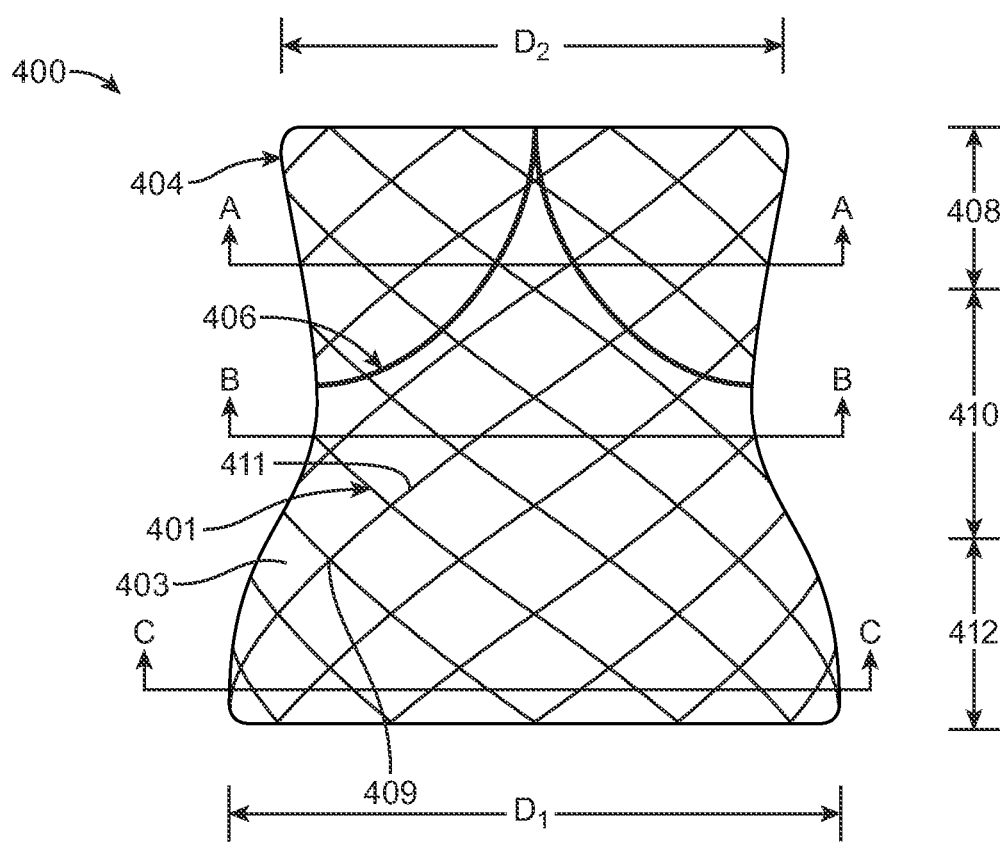
FIG. 5 is a side view of the heart valve prosthesis of FIG. 4, wherein the heart valve prosthesis is depicted in an expanded, deployed configuration.

Stent component 404 may be considered to have three contiguous portions or regions, a proximal portion 412, a distal portion 408, and an intermediate waist portion or midsection 410 extending between proximal and distal portions 412, 408. It will be understood by one of ordinary skill in the art that the length of each portion may vary according to application and is not limited to the proportions shown in FIGS. 4-5. In one embodiment, the length of midsection 410 is approximately equal to the length of a native leaflet of the native valve, which depends upon the type and size of the native valve and may vary between 5 mm and 20 mm. As previously stated FIG. 4 illustrates heart valve prosthesis 400 in a delivery state or configuration, while FIG. 5 illustrates heart valve prosthesis 400 in a deployed state or configuration. In the embodiment depicted in FIGS. 4-5, stent component 404 of valve prosthesis 400 has a cylindrical compressed delivery configuration and an expanded or deployed configuration in which the prosthesis has a profile with an enlarged or flared proximal end 412 that is wider than distal portion 408. Stated another way, proximal portion 412 has nominal deployed diameter $D_1$ and distal portion 408 has nominal deployed diameter $D_2$, which is less than diameter $D_1$. When configured as a replacement for an aortic valve, wider proximal portion 412 functions as an inflow end of heart valve prosthesis 400 and extends into and anchors within the aortic annulus of a patient's left ventricle, while narrower distal portion 408 functions as an outflow end of heart valve prosthesis 400 and is positioned in the patient's ascending aorta.

Figure 4A:
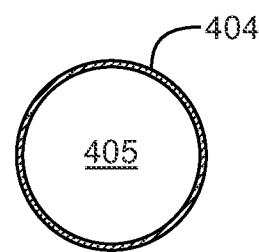
FIG. 4A is a cross-sectional view taken along line A-A of FIG. 4.
Figure 5A:
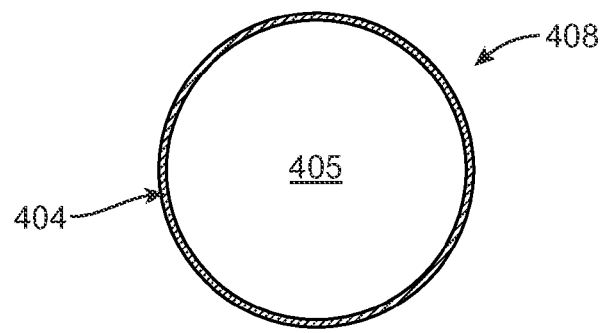
FIG. 5A depicts a cross-sectional view of a support structure of the heart valve prosthesis of FIG. 4 taken along line A-A of FIG. 5.
Figure 5B:
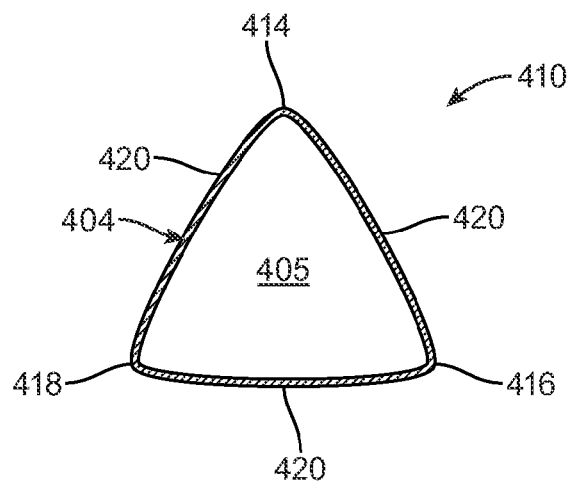
FIG. 5B depicts a cross-sectional view of a support structure of the heart valve prosthesis of FIG. 4 taken along line B-B of FIG. 5.
Figure 5C:
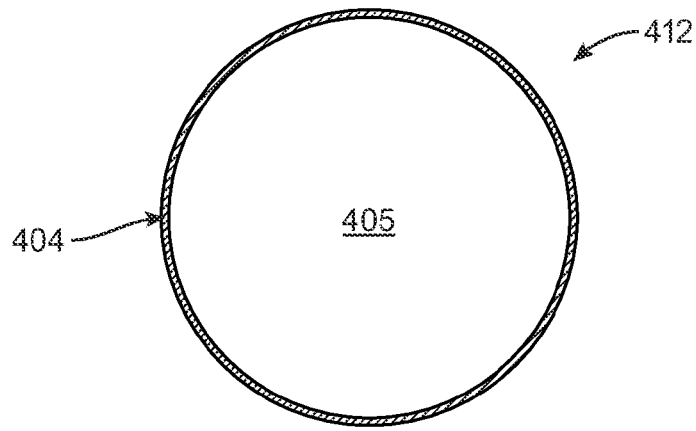
FIG. 5C depicts a cross-sectional view of a support structure of the heart valve prosthesis of FIG. 4 taken along line C-C of FIG. 5.

In the delivery configuration of FIG. 4, tubular stent component 404 has a generally circular cross-section along an entire length as shown in FIG. 4A. As used herein, "generally" circular includes circular, elliptical, or oval shapes. The uniform circular cross-section of tubular stent component 404 in the delivery configuration minimizes the crimped profile of valve prosthesis 400 during delivery. In the deployed configuration of FIG. 5, proximal portion 412 has a generally circular cross-section as shown in FIG. 5A which is configured to be positioned within an annulus portion of the native valve. Intermediate portion 410 has a generally triangular cross-section as shown in FIG. 5B. When positioned in situ, intermediate portion 410 abuts against or is disposed within a leaflet portion of the native valve and the generally triangular cross-section conforms to the surrounding or adjacent tissue of the native valve leaflets. In particular, the generally triangular cross-section includes three vertexes 414, 416, 418 and three segments 420 extending between the vertexes. Vertexes 414, 416, 418 are configured to project into or align with the three commissural points of the native valve leaflets. Distal portion 408 includes prosthetic valve leaflets 407 therein and has a circular cross-section as shown in FIG. 5C. When positioned in situ, distal portion 408 is located distal to the native valve leaflets, which are located adjacent to intermediate portion 410 as described above. In another embodiment hereof (not shown), distal portion 408 may have a generally triangular cross-section and may be configured in situ to abut against or be disposed within the native valve leaflets.

Figure 6A:
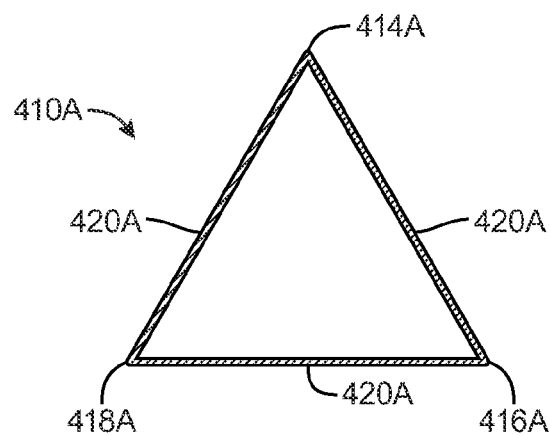
FIGS. 6A-6D illustrate alternate configurations of generally triangular cross-sections of a support structure of the heart valve prosthesis of FIG. 4 according to embodiments hereof.
Figure 6B:
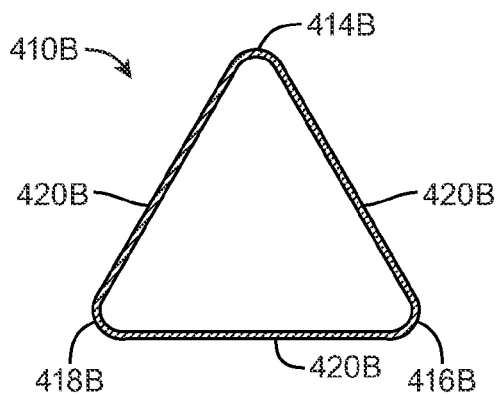
Figure 6C:
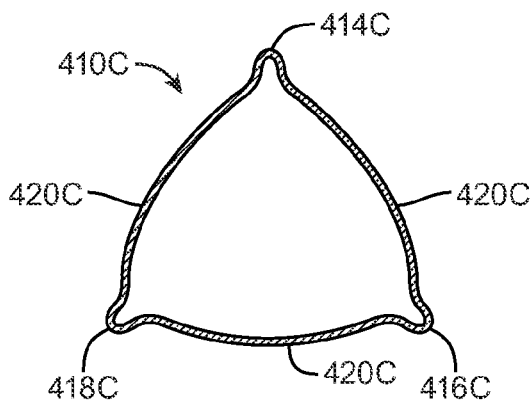
Figure 6D:
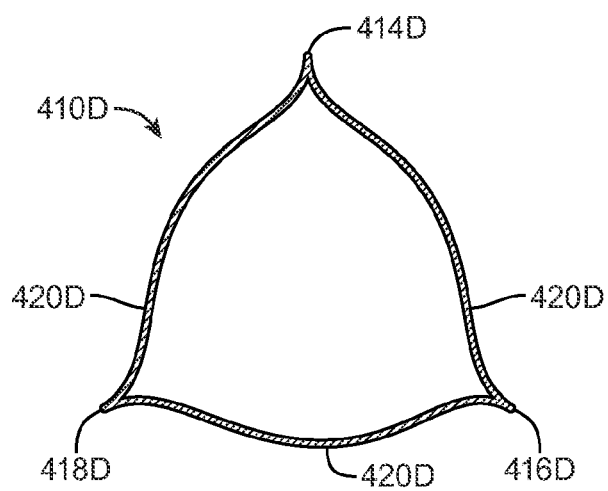

As used herein, "generally" triangular includes: the cross-section of FIG. 5B in which segments 420 of the triangle between adjacent vertexes are slightly rounded and bow outwards in a radial direction; the cross-section of FIG. 6A in which straight segments 420A of the triangle extend between pointed vertexes 414A, 416A, 418A; the cross-section of FIG. 6B in which straight segments 420B of the triangle extend between rounded vertexes 414B, 416B, 418B; the cross-section of FIG. 6C in which curved or radially bowed segments 420C of the triangle extend between elongated curved vertexes 414C, 416C, 418C; and the cross-section of FIG. 6D in which curved or radially bowed segments 420D of the triangle extend between elongated pointed vertexes 414D, 416D, 418D. The generally triangular cross-sections of FIGS. 5B and 6A-6D are generally shown as equilateral triangles but in other embodiments hereof the triangular cross-section may form an isosceles or scalene triangle with right, acute or obtuse angles depending on the anatomy and level of disease of the native heart valve. In any case, the generally triangular cross-section includes three vertexes and three segments therebetween which are configured to be a shape and size that can provide a sealing function for valve prosthesis 400 when the prosthesis is deployed at a native valve target site.

Figure 7:
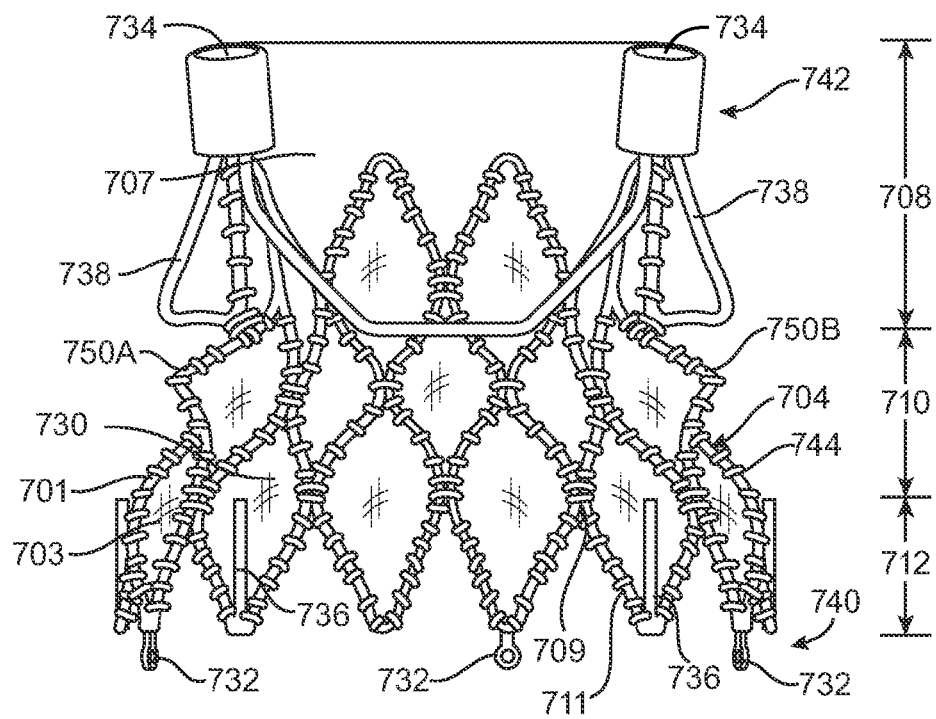
FIG. 7 illustrates a heart valve prosthesis which includes a variable cross-sectional shape along its length to prevent paravalvular leakage according to another embodiment hereof.
Figure 8A:
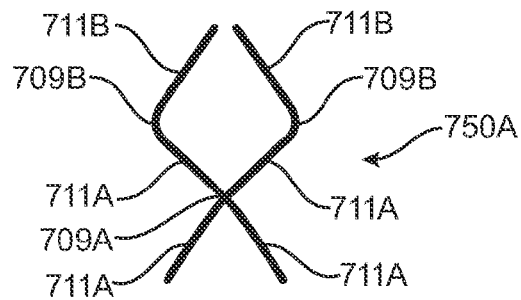
FIG. 8A depicts a portion of a framework of the heart valve prosthesis of FIG. 8 removed from the remainder of the framework for sake of illustration only.
Figure 8:
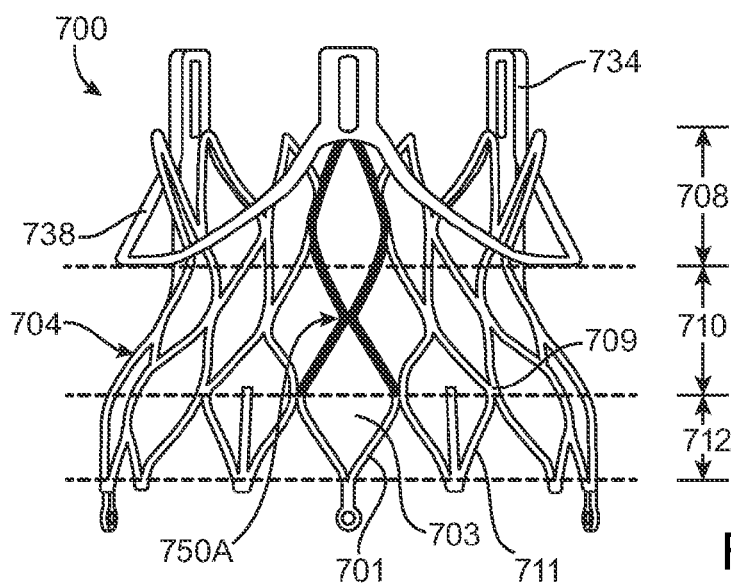
FIGS. 8 and 9 are side and top views, respectively, of the heart valve prosthesis of FIG. 7 with the valve leaflets and graft material removed for clarity purposes.
Figure 9:
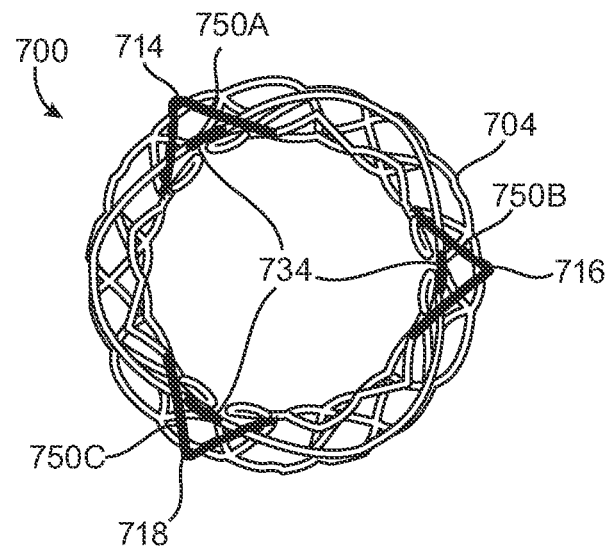

A generally triangular cross-section, as taken or made transverse to a longitudinal axis of a valve prosthesis, is formed by extending particular or selected portions of the stent component framework radially outwards with respect to the rest of framework. A method of forming a generally triangular cross-section on a valve prosthesis is described in more detail with respect to the embodiment depicted in FIGS. 7, 8, and 9. More particularly, FIGS. 7, 8, and 9 illustrate another embodiment hereof in which a heart valve prosthesis 700 is configured for placement in an aortic valve and includes a variable or non-uniform cross-sectional shape along its length to prevent paravalvular leakage. As shown in the side view of FIG. 7, heart valve prosthesis 700 includes a self-expanding tubular stent component or support frame 704, graft material 730 coupled to stent component 704 via a plurality of stitches 744, and valve leaflets 707 located towards a distal outflow end 742 of stent component 704. In one embodiment, heart valve prosthesis 700 may be an Engager™ Aortic Valve Prosthesis from Medtronic Cardio-Vascular, Inc., described in U.S. Patent Application Pub. No. 2010/0262231 to Tuval et al. which is herein incorporated by reference in its entirety, that has been adapted for use as described herein to have a generally triangular cross-section on at least an intermediate portion thereof.

FIGS. 8 and 9 illustrate perspective and top views, respectively, of stent component 704, with valve leaflets 707 and graft material 730 of heart valve prosthesis 700 omitted for clarity. Stent component 704 includes a framework 701 that defines a plurality of diamond-shaped openings 703. Each diamond-shaped opening 703 is defined by four vertexes or vertices 709 and four segments or struts 711 extending or formed between vertexes 709. In this embodiment, framework 701 may be formed by bending or manipulating one or more wires, strands or filaments into the configuration shown in FIG. 8. Stent component 704 includes commissural posts 734 provided at distal end 742 of stent component 704. Heart valve prosthesis 700 is implanted in situ such that, after being expanded to its deployed configuration, the commissural posts 734 are oriented in the native valve in a position corresponding to the commissural points of the native valve leaflets. Stent component 704 further includes three self-expanding support arms 738, which are attached to or formed integrally with stent component 704 towards its distal end 742, and are radially pivotable with respect to an outer surface of stent component 704. Support arms 738, which are visible on fluoroscopic imaging during implantation, assist in accurately positioning or orienting heart valve prosthesis 700 in situ as described in more detail in U.S. Patent Application Pub. No. 2010/0262231 to Tuval et al., previously incorporated by reference. When heart valve prosthesis 700 is implanted in situ, support arms 738 rest on body tissue adjacent to the outflow end of the native valve, thereby bracing or anchoring heart valve prosthesis 700 within the native valve. Stent component 704 may also include three fixation hooks 732 and barbs 736 at a proximal inflow end 740 of stent component 704 for coupling the stent component to a delivery system (not shown).

Similar to other embodiments described herein, stent component 704 defines three contiguous portions or regions including a proximal inflow portion 712, a distal outflow portion 708, and an intermediate waist portion or midsection 710 extending between proximal and distal portions 712, 708. In a compressed or delivery configuration (not shown), stent component 704 has a generally circular cross-section along its length as described above with respect to stent component 404 and FIG. 4A. In the expanded or deployed configuration of prosthesis 700 depicted in FIG. 8, proximal and distal portions 712, 708 have a generally circular cross-section while intermediate portion 710 has a generally triangular cross-section having three vertexes 714, 716, 718.

With reference to FIG. 9, vertexes 714, 716, 718 of the generally triangular cross-section of intermediate portion 710 of valve prosthesis 700 are formed by pulling, pinching or otherwise extending three portions or regions 750A, 750B, 750C of stent component 704 radially outwards and heat setting the stent component. In an embodiment hereof, the manufacture of intermediate portion 710 may be performed with two heat setting steps. More particularly, a generally cylindrical stent is formed with a first heat setting step, three portions or regions 750A, 750B, 750C of stent component 704 are pulled, pinched or otherwise extended radially outwards to form vertexes 714, 716, 718, and an additional, second heat setting step is utilized to set or form intermediate portion 710 in a generally triangular cross-section. In another embodiment hereof, the manufacture of intermediate portion 710 may be performed with one heat setting step. More particularly, a mandrel having an outer surface corresponding to the desired final shape or configuration of the valve prosthesis is inserted into a generally cylindrical stent, which expands or molds into the mandrel shape, and then the mandrel and stent thereon are heat set in a single heating step.

Regardless of whether one or more heat setting steps are utilized in the method of manufacture, the manufacture of intermediate portion 710 includes pulling or extending portions 750A, 750B, 750C of framework 701 out of or away from a cylindrical plane formed by tubular stent component 704. Selected region 750A, which is darkened or bold in FIG. 8 and FIG. 9 for illustrative purposes only, is shown in FIG. 8A removed from the remainder of the framework 701 for illustrative purposes only. Selected portions or regions 750A, 750B, 750C of framework 701 of stent component 704 are proximal to and longitudinally aligned with commissural posts 734, and are configured to be oriented in situ in a position corresponding to or adjacent to the commissural points of the native valve leaflets. Accordingly, vertexes 714, 716, 718 configured to project into or align with the three commissural points of the native valve leaflets. Selected portions or regions 750A, 750B, 750C of framework 701 include a vertex 709A of framework 701 and four struts 711A that extend or radiate from the selected vertex 409A in an "X" configuration. When vertex 709A and struts 711A are pulled or otherwise extended outwards, additional vertexes and/or struts of framework 701 that are near or adjacent to vertex 709A and struts 711A may also be slightly pulled or extended radially outwards but vertex 709A of framework 701 forms one of vertexes 714, 716, 718 of the generally triangular cross-section. For example, in the embodiment of FIG. 8, vertexes 709B and struts 711B which are adjacent to struts 711A may be slightly pulled or extended radially outwards when vertex 709A is pulled or extended radially outwards because in this embodiment vertexes 709B are not coupled to other adjacent vertexes of framework 701.

Delivery of heart valve prosthesis 700, or a heart valve prosthesis according to any embodiment hereof, may be accomplished with a delivery catheter (not shown). During delivery, the heart valve prosthesis remains in its compressed delivery configuration until it reaches a target diseased native heart valve, at which time the heart valve prosthesis can be released from the delivery catheter in situ to self-expand to the deployed configuration. The delivery catheter is then removed and the heart valve prosthesis remains deployed within the native target heart valve. In another embodiment hereof, a heart valve prosthesis according to any embodiment described herein may be balloon-expandable and a balloon catheter may be utilized for expanding the heart valve prosthesis to the deployed configuration. The balloon catheter may include a non-cylindrical balloon at its distal end for expanding the heart valve prosthesis. In one embodiment, the non-cylindrical balloon includes at least two contiguous portions or regions, a first portion having a generally triangular cross-section and a second portion having a generally circular cross-section, which correspond to and align with the portions of the heart valve prosthesis having generally triangular and circular cross-sections, respectively, for expanding the prosthesis to its final deployed configuration.

Fluoroscopy can be used to assist in orientation of the heart valve prosthesis in situ. Precise rotational positioning/orientation of heart valve prosthesis 700 allows a clinician to position vertexes 714, 716, 718 of the generally triangular cross-section into the native commissure points of the native valve leaflets. In an embodiment hereof, the heart valve prosthesis and/or the delivery system may include one or more features to identify the orientation of the heart valve prosthesis on fluoroscopic image. In one embodiment hereof, delivery of a heart valve prosthesis according to any embodiment hereof may be accomplished via a percutaneous transfemoral approach and the delivery system may include a rotational identifier that identifies the rotational orientation of the heart valve prosthesis in situ, as described in more detail in U.S. Patent Application Pub. No. 2012/0158129 to Duffy et al., herein incorporated by reference in its entirety. In another embodiment hereof, delivery of a heart valve prosthesis according to any embodiment hereof may be accomplished via a transapical approach directly through the apex of the heart via a thoracotomy or by other close range transcatheter delivery methods. A transapical approach requires a relatively shorter length of catheter, as compared to a percutaneous transfemoral approach, and therefore may allow heart valve prosthesis 700 to be more accurately oriented in the native valve, as described in more detail in U.S. Patent Application Pub. No. 2010/0262231 to Tuval et al. previously incorporated by reference. Other techniques for assisting in rotational positioning/orientation of heart valve prosthesis 700 include pre-implant planning via computed tomography (CT) or other imaging modalities, image fusion technologies for transcatheter aortic-valve implantation (TAVI), and/or utilization of electromagnetic sensors or accelerometers.

Figure 10:
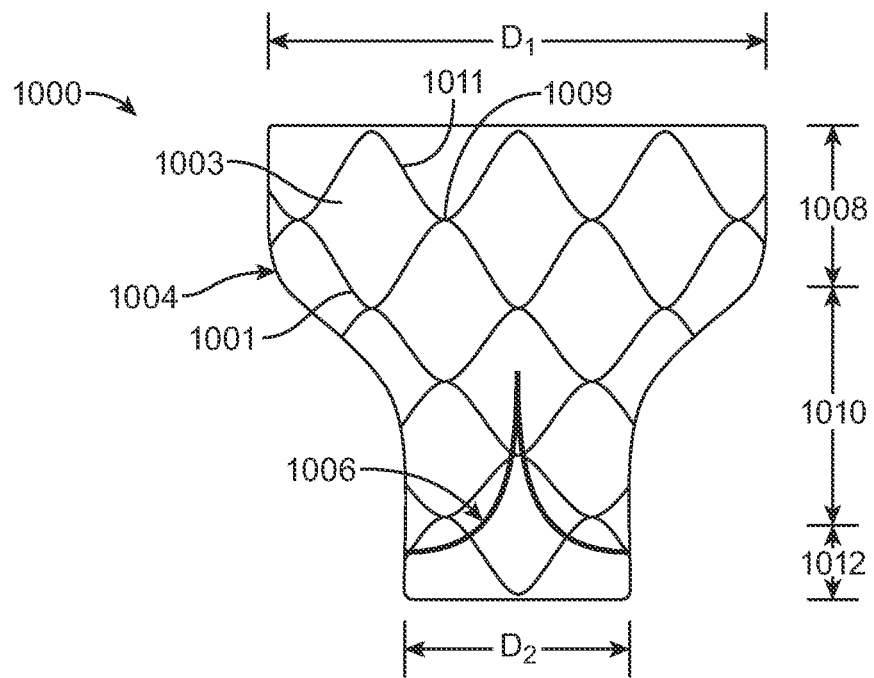
FIG. 10 is a side view of a heart valve prosthesis according to another embodiment hereof, wherein the heart valve prosthesis is depicted in an expanded, deployed configuration in which the prosthesis has a profile with an enlarged or flared end.

It is would be understood by one of ordinary skill in the art upon reading the entire disclosure hereof that any number of alternate heart valve prostheses may be adapted for use in embodiments hereof to include a generally triangular cross-section to prevent paravalvular leakage and the location of the generally triangular cross-section along the length of heart valve prosthesis may vary according to the configuration thereof. For example, FIG. 10 illustrates a heart valve prosthesis 1000 including a self-expanding tubular stent component or support frame 1004 and a prosthetic valve component 1006 secured within stent component 1004. Stent component 1004 includes a framework 1001 that defines a plurality of diamond or kite-shaped openings 1003. Each diamond-shaped opening 1003 is defined by four vertexes or vertices 1009 and four segments or struts 1011 extending or formed between vertexes 1009. In this embodiment, framework 1001 is formed from a plurality of sinusoidal rings that are coupled together at the bends or apexes of the sinusoid to form diamond-shaped openings 1003. Similar to the embodiments described above, stent component 1004 includes a proximal inflow portion 1012, a distal outflow portion 1008, and an intermediate waist portion or midsection 1010. Stent component 1004 of valve prosthesis 1000 has a cylindrical compressed or delivery configuration (not shown but as described above with respect to stent component 404 and FIG. 4A) and a deployed configuration (shown in FIG. 10) in which the prosthesis has a profile with an enlarged or flared distal portion 1008 that is wider than proximal portion 1012. Distal portion 1008 has nominal deployed diameter $D_1$ and proximal portion 1012 has nominal deployed diameter $D_2$, which is less than diameter $D_1$. When configured as a replacement for an aortic valve, proximal portion 1012 functions as an inflow end of heart valve prosthesis 1000 and extends into and is positioned within the aortic annulus of a patient's left ventricle, while distal portion 1008 functions as an outflow end of heart valve prosthesis 1000 and is positioned in the patient's ascending aorta.

In the expanded or deployed configuration of FIG. 10, proximal and distal portions 1012, 1008 have generally circular cross-sections while intermediate portion 1010 has a generally triangular cross-section. The generally triangular cross-section of intermediate portion 1010, which in this embodiment also includes prosthetic valve component 1006 secured therein, is configured to be positioned in situ such that it abuts against or is adjacent to the commissural points of the native valve leaflets. Proximal portion 1012 having a generally circular cross-section is configured to be positioned within an annulus portion of the native valve, and distal portion 1008 having a generally circular cross-section is located distal to the native valve leaflets. In one embodiment, heart valve prosthesis 1000 may be a CoreValve™ valve prosthesis from Medtronic CardioVascular, Inc., described in U.S. Patent Application Pub. No. 2011/0172765 to Nguyen et al. which is herein incorporated by reference in its entirety, that has been adapted for use as described herein to have a generally triangular cross-section on at least an intermediate portion thereof.

Figure 11:
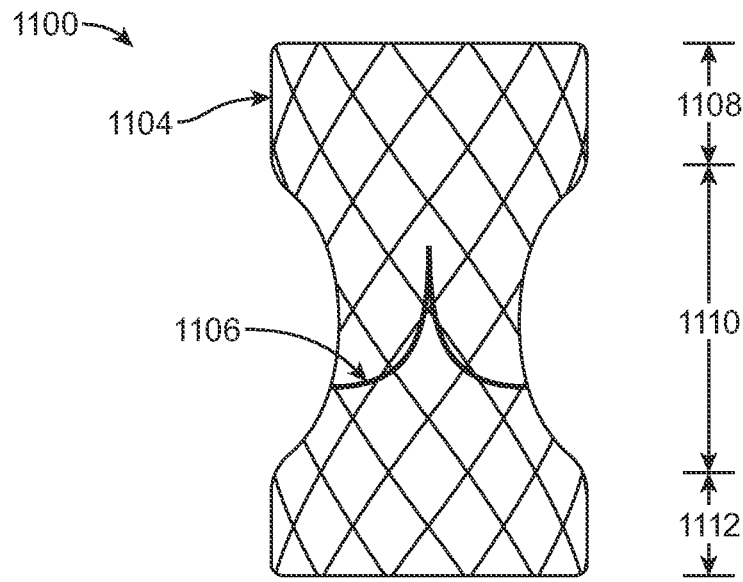
FIG. 11 is a side view of a heart valve prosthesis according to another embodiment hereof, wherein the heart valve prosthesis is depicted in an expanded, deployed configuration in which the prosthesis has an hourglass profile.
Figure 12:
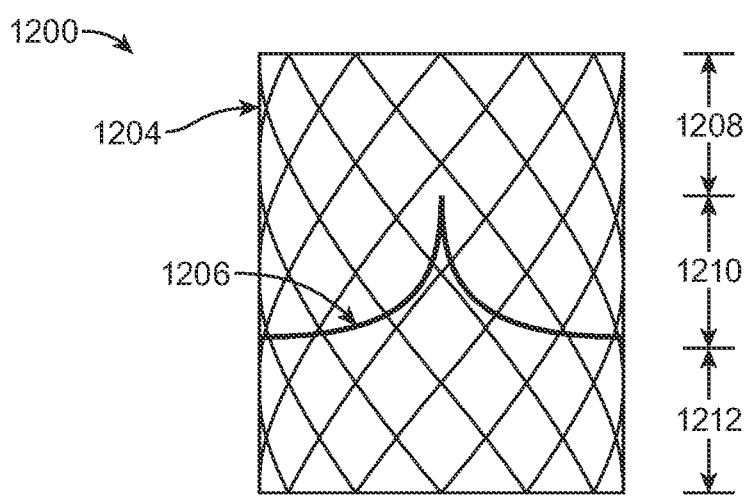
FIG. 12 is a side view of a heart valve prosthesis according to another embodiment hereof, wherein the heart valve prosthesis is depicted in an expanded, deployed configuration in which the heart valve prosthesis has a generally straight profile.

FIGS. 11 and 12 illustrate alternative configurations of heart valve prostheses having a variable cross-sectional shape along their lengths to prevent paravalvular leakage. As alternatives to the deployed configurations described above, the stent component/valve support frame may have a deployed configuration in which the prosthesis has an hourglass profile, a deployed configuration in which the prosthesis has a generally straight profile, or other stent configuration or shape known in the art for valve replacement. The stent component may be designed with a number of different configurations and sizes to meet the different requirements of the location in which it may be implanted.

For example, FIG. 11 illustrates a heart valve prosthesis 1100 having a deployed configuration in which the prosthesis has an hourglass profile. Heart valve prosthesis 1100 includes a self-expanding tubular stent component or support frame 1104 and a prosthetic valve component 1106 secured within stent component 1104. Stent component 1104 has a cylindrical compressed delivery configuration (not shown but as described above with respect to stent component 404 and FIG. 4A) and a deployed configuration (shown in FIG. 11) in which proximal and distal portions 1112, 1108 have a generally circular cross-section while an intermediate portion 1110 has a generally triangular cross-section which is configured to be positioned in situ such that it abuts against or is adjacent to the commissural points of the native valve leaflets. In the deployed configuration of FIG. 11, distal portion 1108 has approximately the same nominal deployed diameter as proximal portion 1112, with intermediate portion 1110 being contracted or narrowed relative to distal and proximal portions 1108, 1112. Thus, the deployed width of intermediate portion 1110 having a generally triangular cross-section is less than the deployed diameter of proximal and distal portions 1112, 1108 having generally circular cross-sections that are approximately equal.

FIG. 12 illustrates a heart valve prosthesis 1200 having a deployed configuration in which the prosthesis has a generally straight profile. Heart valve prosthesis 1200 is similar to heart valve prosthesis 1100 described herein except that the intermediate portion of prosthesis 1200 is not contracted or narrowed relative to the distal and proximal portions thereof. More particularly, similar to embodiments described above, heart valve prosthesis 1200 includes a self-expanding tubular stent component or support frame 1204 and a prosthetic valve component 1206 secured within stent component 1204. Stent component 1204 has a cylindrical compressed or delivery configuration (not shown but as described above with respect to stent component 404 and FIG. 4A) and a deployed configuration (shown in FIG. 12) in which proximal and distal portions 1212, 1208 have a generally circular cross-section while an intermediate portion 1210 has a generally triangular cross-section which is configured to be positioned in situ such that it abuts against or is adjacent to the commissural points of the native valve leaflets. In the deployed configuration of FIG. 12, distal portion 1208 has approximately the same nominal deployed diameter as proximal portion 1212. Further, the deployed width of intermediate portion 1210 having a generally triangular cross-section is approximately equal to the deployed diameters of proximal and distal portions 1212, 1208 having generally circular cross-sections.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising: a tubular stent component having a framework defining a lumen therethrough and having a compressed delivery configuration for transcatheter delivery within a vasculature and a deployed configuration for implantation within a native heart valve, wherein the framework has a generally circular cross-section along its length when in the delivery configuration and wherein the framework includes a first portion having a generally circular cross-section, a second portion having a generally triangular cross-section, and a third portion having a generally circular cross-section, the second portion being positioned between the first and third portions; and a prosthetic valve component disposed within and secured to the framework.

2. The transcatheter valve prosthesis of claim 1, wherein the framework of the generally triangular cross section includes three vertexes that are configured to project into three commissural points of a native valve when the valve prosthesis is implanted in situ.

3. The transcatheter valve prosthesis of claim 2, wherein the framework of the circular cross-section is configured to be positioned within an annulus portion of the native valve when the valve prosthesis is implanted in situ.

4. The transcatheter valve prosthesis of claim 1, wherein the stent component is self-expanding.

5. The transcatheter valve prosthesis of claim 1, wherein the prosthetic valve component includes three valve leaflets.

6. The transcatheter valve prosthesis of claim 1, wherein the prosthetic valve component is disposed within the framework of the third portion of the stent component.

7. The transcatheter valve prosthesis of claim 1, wherein a deployed diameter of the first portion is greater than a deployed diameter of the third portion.

8. The transcatheter valve prosthesis of claim 1, wherein a deployed diameter of the first portion is approximately the same as a deployed diameter of the third portion.

9. The transcatheter valve prosthesis of claim 8, wherein the second portion has a deployed width that is less than the deployed diameters of the first and third portions.

10. The transcatheter valve prosthesis of claim 8, wherein the second portion has a deployed width that is approximately the same as the deployed diameters of the first and third portions.

11. The transcatheter valve prosthesis of claim 1, further comprising: commissural posts coupled to or extending from a distal end of the framework, wherein the framework of the generally triangular cross-section includes three vertexes that are proximal to and longitudinally aligned with the commissural posts.

12. The transcatheter valve prosthesis of claim 1, further comprising:
at least one self-expanding support arm coupled to a distal end of the stent component, wherein the at least one support arm is operable to pivot radially with respect to the stent component.

13. The transcatheter valve prosthesis of claim 1, wherein the prosthetic valve component is disposed within the framework of the second portion of the stent component.

14. A transcatheter valve prosthesis comprising: a tubular self-expanding stent component having a framework defining a lumen therethrough and having a deployed configuration for implantation within a native heart valve, the framework having a proximal portion, a distal portion, and an intermediate portion between the proximal and distal portions, wherein the framework has a variable shaped cross-section when in the deployed configuration in which at least the intermediate portion has a generally triangular cross-section with three vertexes that are configured to project into three commissural points of a native valve when the valve prosthesis is implanted in situ and wherein the proximal and distal portions have a generally circular cross-section when in the deployed configuration; and a prosthetic valve component disposed within and secured to the stent component, wherein the prosthetic valve component includes three valve leaflets.

15. The transcatheter valve prosthesis of claim 14, wherein the proximal portion is configured to be positioned within an annulus portion of the native valve when the valve prosthesis is implanted in situ.

16. The transcatheter valve prosthesis of claim 14, wherein a deployed diameter of the proximal portion is greater than a deployed diameter of the distal portion.

17. The transcatheter valve prosthesis of claim 14, wherein a deployed diameter of the distal portion is greater than a deployed diameter of the proximal portion.

18. The transcatheter valve prosthesis of claim 14, wherein the prosthetic valve component is disposed within the framework of the intermediate portion of the stent component.

* * * * *